(12) United States Patent
Henderson et al.

(10) Patent No.: US 12,151,039 B2
(45) Date of Patent: Nov. 26, 2024

(54) SANITATION DEVICE

(71) Applicant: Handle Halo LLC, Redmond, WA (US)

(72) Inventors: Travis Henderson, Redmond, WA (US); Colin Jacob Miller, Seattle, WA (US); Justin Matthew Knowles, Seattle, WA (US); Timothy Mark Christman, Seattle, WA (US)

(73) Assignee: Handle Halo LLC, Redmond, WA (US)

( * ) Notice: Subject to any disclaimer, the term of this patent is extended or adjusted under 35 U.S.C. 154(b) by 406 days.

(21) Appl. No.: 17/837,698

(22) Filed: Jun. 10, 2022

(65) Prior Publication Data
US 2022/0395599 A1 Dec. 15, 2022

Related U.S. Application Data

(60) Provisional application No. 63/209,340, filed on Jun. 10, 2021.

(51) Int. Cl.
*A61L 2/10* (2006.01)
(52) U.S. Cl.
CPC ............ *A61L 2/10* (2013.01); *A61L 2202/11* (2013.01); *A61L 2202/122* (2013.01); *A61L 2202/14* (2013.01)

(58) Field of Classification Search
CPC .......... A61L 2/10; A61L 2/24; A61L 2202/11; A61L 2202/122; A61L 2202/14; A61L 2202/16
See application file for complete search history.

(56) References Cited

U.S. PATENT DOCUMENTS

| | | | |
|---|---|---|---|
| 2022/0054696 A1* | 2/2022 | Huang | G01P 13/00 |
| 2022/0193298 A1* | 6/2022 | Collet | A61L 9/20 |
| 2022/0241447 A1* | 8/2022 | Ghalili | A61L 2/24 |

FOREIGN PATENT DOCUMENTS

WO WO-2017048877 A1 * 3/2017 ............... A61L 2/10

* cited by examiner

*Primary Examiner* — David E Smith
(74) *Attorney, Agent, or Firm* — Seed IP Law Group LLP

(57) ABSTRACT

A sanitation device includes a housing with a channel extending into the housing and a plurality of openings in the channel. A plurality of light emitting diodes emit light through the openings in the channel. A shield is coupled to the housing and a motion sensor emits and detect light through the shield when activated, such that the shield narrows a field of view of the motion sensor. The sanitation device is positioned near a common touch point with the motion sensor determining when an object is near, and has moved away from, the touch point. The plurality of light emitting diodes are activated to clean the touch point after the object moves away. The sanitation device may further include a status indicator light to provide information regarding the current state of operation of the sanitation device.

20 Claims, 10 Drawing Sheets

SANITATION DEVICE

BACKGROUND

Technical Field

The present disclosure relates to a sanitation device, and more particularly, to a sanitation device that uses light to disinfect common touch points between repeated uses.

Description of the Related Art

Sanitation devices are known and include items such as chemical sprays and wipes. However, sprays and wipes are not easily adapted for use with common touch points that are known to be a source of viral or bacterial transmission. In other words, it is impractical to use a spray or wipe to clean a surface such as a door handle in a high occupancy space after each and every use. Such repeated cleaning with these products also produces waste that is harmful to the environment and may wear down surfaces over time.

Various wavelengths of light have been researched as an alternative to using chemical sprays and wipes and have been found to be more applicable in certain use cases. However, the wavelengths of light used to clean surfaces are potentially harmful to human skin and eyes. Moreover, known devices that produce light in wavelengths that will clean a surface utilize an external power source, which limits applicability where power is not readily available.

As a result, it would be advantageous to have sanitation devices, systems, and methods that overcome the disadvantages of known sanitation devices.

BRIEF SUMMARY

Embodiments of the present disclosure broadly include a sanitation device with a housing with a channel extending into the housing and a plurality of openings in the channel. A plurality of light emitting diodes emit light through the openings in the channel. A shield is coupled to the housing. A motion sensor is able to detect light through the shield, such that the shield narrows a field of view of the motion sensor. The sanitation device is positioned near a common touch point with the motion sensor determining when an object is near, and has moved away from, the touch point. The plurality of light emitting diodes are activated to clean the touch point after the object moves away. The sanitation device may further include a status indicator light to provide information regarding the current state of operation of the sanitation device and common touch point, such as clean, dirty, and cleaning.

One or more embodiments of a sanitation device according to the present disclosure may be summarized as including: a housing including a cavity and a cover rotatably coupled to the body to selectively provide access to the cavity; a channel extending into the housing; a plurality of openings in the channel; a plurality of light emitting diodes coupled to the housing that emit light through the plurality of openings in the channel when activated; a shield coupled to the housing with at least a portion of the shield extending from the channel; an aperture in the shield; and a motion detection sensor coupled to the housing that is able to detect light through the aperture in the shield.

The sanitation device may further include: the housing further including a battery terminal with at least one battery received in the battery terminal; the cover of the housing being rotatable to selectively provide access to the battery terminal for replacement of the at least one battery; control circuitry including a memory and a processor coupled to the housing and positioned in the cavity of the housing, the control circuitry in electronic communication with the at least one battery, the plurality of light emitting diodes, and the motion detection sensor; the processor executing instructions stored in the memory that cause the control circuitry to activate the motion detection sensor, determine whether an object is proximate the motion detection sensor at a first instance in time based on the differences in light emitted and detected by the motion detection sensor, determine when the object has moved away from the motion detection sensor at a second instance in time, activate the plurality of light emitting diodes for a set period of time in response to the determination that the object has moved away from the motion detection sensor at the second instance, and deactivate the plurality of light emitting diodes after the set period of time.

The sanitation device may further include: a status indication slot in the cover, a status indicator light coupled to the housing that is able to emit light through the status indication slot in the cover, the status indicator light in electronic communication with the control circuitry; the processor executing instructions stored in the memory that cause the control circuity to activate the status indicator light and emit light from the status indicator light in a first color before the first instance, activate the status indicator light to emit light in a second different color when the object is proximate the motion detector, activate the status indicator light to emit light in a third different color upon activation of the plurality of light emitting diodes and during the set period of time, and activate the status indicator light to emit light in the first color after deactivation of the plurality of light emitting diodes after the set period of time.

The sanitation device may further include: the housing including a bottom surface, the channel recessed into the bottom surface of the housing with sidewalls of the channel narrowing a field of emission of the plurality of light emitting diodes; the channel having a base and the plurality of light emitting diodes being angled relative to the base of the channel; an outer peripheral edge of the shield extending further from the housing than an outer peripheral edge of the motion detection sensor to narrow a field of view of the motion detection sensor; and the motion detection sensor being tuned to trigger based on detection of an object within a predetermined range of proximity to the motion detection sensor.

The sanitation device may further include: a safety shut-off sensor in electronic communication with the control circuitry, and a safety shut-off switch in electronic communication with the safety-shutoff sensor and the control circuitry; the processor executing instructions stored in the memory that cause the control circuity to activate the safety shut-off sensor during operation of the plurality of light emitting diodes, detect with the safety shut-off sensor whether an object is proximate the safety shut-off sensor during operation of the plurality of light emitting diodes, and activate the safety shut-off switch to deactivate the plurality of light emitting diodes upon detection that the object is proximate the safety shut-off sensor during operation of the plurality of light emitting diodes; and the motion detection sensor including the safety shut-off sensor.

One or more embodiments of a sanitation device according to the present disclosure may be summarized as including: a housing; a channel extending into the housing; a plurality of light emitting diodes coupled to the housing and operable to emit light from the channel; a shield coupled to the housing and positioned in the channel, the shield including an aperture; and a motion detection sensor coupled to the housing and operable to detect light through the aperture in the shield.

The sanitation device may further include: the housing including a cavity, and the sanitation device further including a plurality of openings in the channel, the plurality of light emitting diodes operable to emit light through the plurality of openings in the channel, and a cover rotatably coupled to the housing to selectively provide access to the cavity of the housing; and control circuitry including a memory and a processor coupled to the housing, the control circuitry in electronic communication with the plurality of light emitting diodes and the motion detection sensor, wherein the processor executes instructions stored in the memory that cause the control circuitry to activate the motion detection sensor, determine whether an object is proximate the motion detection sensor at a first instance in time based on the differences in light emitted and detected by the motion detection sensor, determine when the object has moved away from the motion detection sensor at a second instance in time, activate the plurality of light emitting diodes for a set period of time in response to the determination that the object has moved away from the motion detection sensor at the second instance, and deactivate the plurality of light emitting diodes after the set period of time.

The sanitation device may further include: a status indication slot in the cover; and a status indicator light coupled to the housing, wherein the status indicator light emits light through the status indication slot in the cover, the status indicator light in electronic communication with the control circuitry, wherein the processor executes instructions stored in the memory that cause the control circuity to activate the status indicator light and emit light from the status indicator light in a first color before the first instance, activate the status indicator light to emit light in a second different color when the object is proximate the motion detector, activate the status indicator light to emit light in a third different color upon activation of the plurality of light emitting diodes and during the set period of time, and activate the status indicator light to emit light in the first color after deactivation of the plurality of light emitting diodes after the set period of time; a safety shut-off sensor in electronic communication with the control circuitry, and a safety shut-off switch in electronic communication with the safety-shutoff sensor and the control circuitry, wherein the processor executes instructions stored in the memory that cause the control circuity to activate the safety shut-off sensor during operation of the plurality of light emitting diodes, detect with the safety shut-off sensor whether an object is proximate the safety shut-off sensor during operation of the plurality of light emitting diodes, and activate the safety shut-off switch to deactivate the plurality of light emitting diodes upon detection that the object is proximate the safety shut-off sensor during operation of the plurality of light emitting diodes.

The sanitation device may further include: the housing including a bottom surface, the channel recessed into the bottom surface of the housing with sidewalls of the channel narrowing a field of emission of the plurality of light emitting diodes, and the channel having a base and the plurality of light emitting diodes are angled relative to the base of the channel.

BRIEF DESCRIPTION OF THE SEVERAL VIEWS OF THE DRAWINGS

The present disclosure will be more fully understood by reference to the following figures, which are for illustrative purposes only. These non-limiting and non-exhaustive embodiments are described with reference to the following drawings, wherein labels refer to corresponding components throughout the various views unless otherwise specified. The sizes and relative positions of elements in the drawings are not necessarily drawn to scale in some figures. For example, the shapes of various elements are selected, enlarged, and positioned to improve drawing legibility. In other figures, the sizes and relative positions of elements in the drawings are exactly to scale. The particular shapes of the elements as drawn may have been selected for ease of recognition in the drawings. The figures do not describe every aspect of the teachings disclosed herein and do not limit the scope of the claims.

DETAILED DESCRIPTION

Persons of ordinary skill in the relevant art will understand that the present disclosure is illustrative only and not in any way limiting. Other embodiments of the presently disclosed systems and methods readily suggest themselves to such skilled persons having the assistance of this disclosure.

Each of the features and teachings disclosed herein can be utilized separately or in conjunction with other features and teachings to provide sanitation devices, systems, and methods. Representative examples utilizing many of these additional features and teachings, both separately and in combination, are described in further detail with reference to attached FIGS. 1-11. This detailed description is merely intended to teach a person of skill in the art further details for practicing aspects of the present technology and is not intended to limit the scope of the claims. Therefore, combinations of features disclosed in the detailed description may not be necessary to practice the teachings in the broadest sense, and are instead taught merely to describe particularly representative examples of the present teachings.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help understand how the present teachings are practiced, but are not intended to limit the dimensions and the shapes shown in the examples in some embodiments. In some embodiments, the dimensions and the shapes of the components shown in the figures are exactly to scale and intended to limit the dimensions and the shapes of the components.

The present disclosure is generally directed to sanitation devices that utilize light with wavelengths in the ultraviolet (UV) range to disinfect common touch points between uses. Although the drawings depict a sanitation device provided in two example form factors, it is to be appreciated the concepts of the disclosure can be applied broadly to a number of different form factors. Further, certain non-limiting examples of a cleaning process are provided with respect to a toilet handle. It is to be appreciated that the sanitation device and systems of the present disclosure can also be used in a number of different ways and with any common touch point, such as by way of example only, and not by way of limitation, with door handles, key pads, railings, elevator buttons, writing implements or utensils, touch screens, and others.

Figure 1:
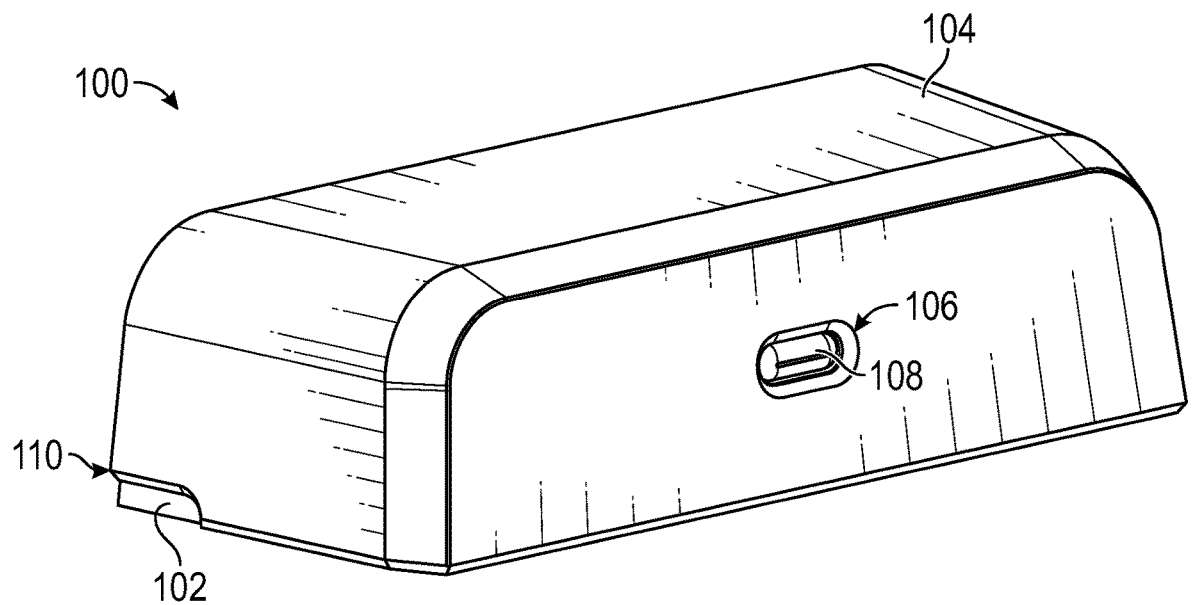
FIG. 1 is a front isometric view of an embodiment of a sanitation device with a cover in a closed position according to the present disclosure.
Figure 2:
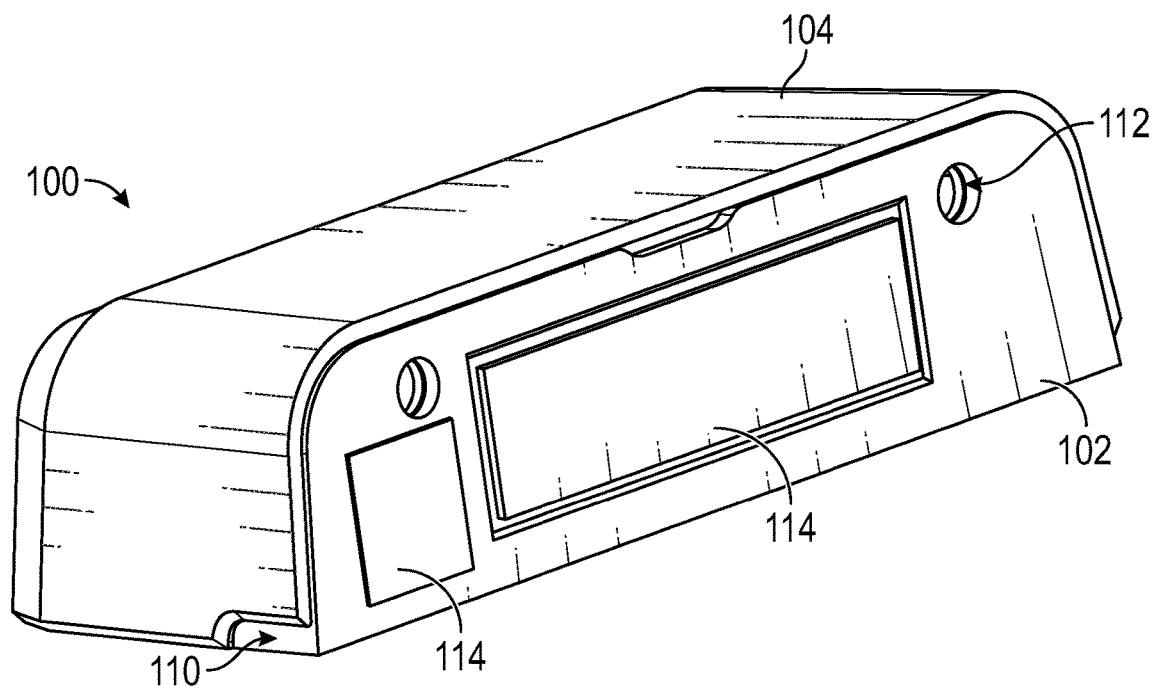
FIG. 2 is a rear isometric view of the sanitation device of FIG. 1.

FIG. 1 depicts a front isometric view of an embodiment of a sanitation device 100 and FIG. 2 depicts a rear isometric view of the sanitation device 100. The sanitation device 100 may be coupled to a lid or other portion of a toilet and is positioned to emit light onto a handle of the toilet to disinfect the handle of the toilet between uses, as described further herein. The sanitation device 100 may also be coupled to support structures proximate other common touch points, as above.

With reference to FIG. 1 and FIG. 2, the sanitation device 100 includes a housing 102 and a cover 104 that is rotatably coupled to the housing 102 to selectively provide access to an internal area of the housing 102. FIG. 1 and FIG. 2 show the cover 104 of the housing 102 in a closed position with access to the internal area of the housing 102 restricted by the cover 104. As best shown in FIG. 1, the cover 104 includes a status indication slot 106 and a status indicator light 108. The status indicator light 108 is coupled to the housing 102 and operable to emit light through the status indicator slot 106. The status indicator slot 106 may be positioned on a front surface of the cover 104 and provided in a form of an opening or aperture corresponding in size and shape to the status indicator light 108. In a non-limiting example, the status indicator slot 106 and the status indicator light 108 are positioned centrally on the front surface of the cover 104, although the same is not necessarily required. The status indicator light 108 may be a light-emitting diode ("LED") or some other type of light source that, when activated, emits light in the visible spectrum. In particular, the status indicator light 108 is operable to emit light in selected colors that correspond to operational states of the sanitation device 100, as further described herein. The cover 104 may also include one or more cutouts 110 located at an interface with the housing 102, and more particularly, at an edge of the cover 104 and/or the housing 102 to assist with manipulating the cover 104 between open and closed positions. Such cutouts 110 may be located at the left and right top and/or bottom corners of the device 100, or along top and bottom edges of the device 100.

The housing 102 may also include mounting holes 112 best shown in FIG. 2. The mounting holes 112 extend through selected locations on the rear surface of the housing 102 to enable the device 100 to be coupled to different support structures or surfaces with fasteners, where applicable. The housing 102 may also include one or more adhesive strips 114 on the rear surface of the housing 102 to assist with coupling the device 100 to support structures or surfaces where it would otherwise be impractical to use fasteners, such as to a porcelain toilet.

Figure 3:
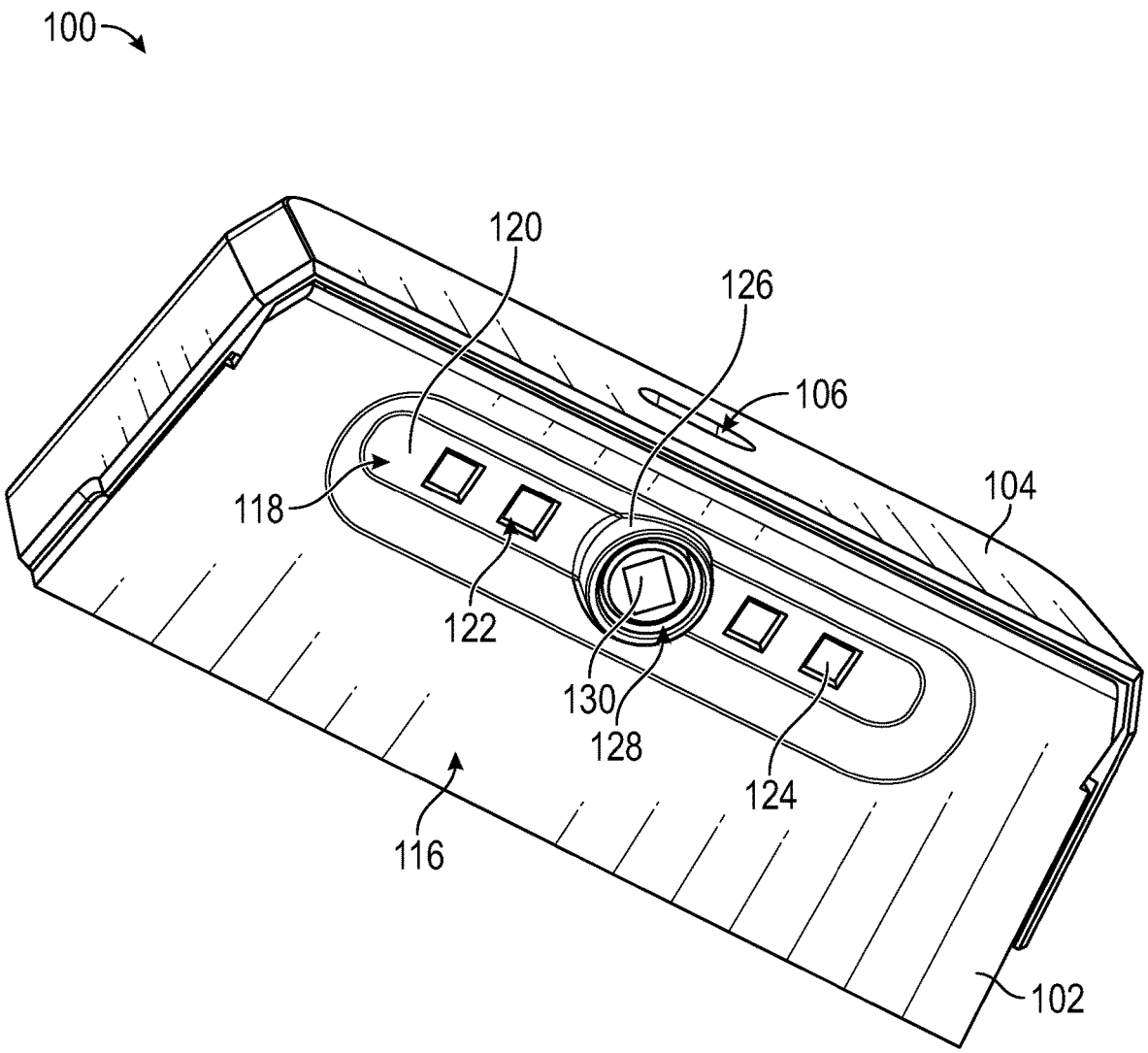
FIG. 3 is a bottom isometric view of the sanitation device of FIG. 1.

Turning to FIG. 3, the housing 102 further includes a bottom surface 116 and a channel 118 extending into or otherwise recessed into the bottom surface 116 of the housing 102. The channel 118 may be positioned closer to a front surface of the sanitation device 100 (i.e., the front surface of the cover 104) than a rear surface of the sanitation device 100 (i.e., the rear surface of the housing 102) in some embodiments to better align light output by the device 100 with the common touch point. Further, the channel 118 may have continuously angled, sloped, curved, or tapered sidewalls from the bottom surface 116 of the housing 102 to a base 120 of the channel 118 such that a width of the channel 118 at the bottom surface 116 of the housing 102 is greater than a width of the channel 118 at the base 120 of the channel 118. The sanitation device 100 further includes a plurality of openings 122 in the base 120 of the channel 118. Although four openings 122 are shown, the number of openings 122 can be more or less than four and may be selected according to design factors. A plurality of LEDs 124 are coupled to the housing 102 and are structured or positioned to emit light through the openings 122. Further, the LEDs may be angled and recessed relative to the openings 122 and the channel 118 to reduce light leakage, which reduces the risk of harm from the light of the LEDs 124 to smaller humans and animals, or to those who are sensitive to particular wavelengths of light. In some embodiments, the LEDs 124 are UV-C LEDs that emit light in wavelengths between 200 and 290 nanometers, or more or less, and are capable of killing a variety of bacteria and viruses.

The sanitation device 100 further includes a shield 126 coupled to the housing 102. More specifically, the shield 126 is coupled to the housing 102 at the base 120 of the channel 118 and extends from a center of the channel 118 in a direction away from the base 120 of the channel 118 in some embodiments. As a result, the shield 126 extends, at least in part, from or through the channel 118. The shield 126 may have a hollow cylindrical shape with an aperture or opening 128 at both ends, or in other words, may include a longitudinal axial bore through the shield 126. In some embodiments, the shield 126 has a different shape. As shown in FIG. 3, the LEDs 124 may be arranged in equal numbers on opposite sides of the shield 126 with equal spacing between the LEDs. However, the number and arrangement of the LEDs relative to the shield 126 may be selected to be different than that shown.

A motion detection sensor 130 is coupled to the housing 102 and is able to detect light through the aperture 128 in the shield 126. In an embodiment, the motion detector sensor 130 is recessed with respect to the aperture 128 in the shield 126, or an outer peripheral edge of the shield 126 extends further from the housing 102 than an outer peripheral edge of the motion detection sensor 130. Thus, the motion detection sensor 130 may be positioned in or have a field of view through the shield 126 with the shield 126 narrowing the field of view of the motion detection sensor 130 to prevent false readings or detection of motion that is not associated with a common touch point.

The motion detection sensor 130 may be a passive infrared ("PIR") sensor that measures infrared light radiating from objects in its field of view to detect motion. Further, the motion detection sensor 130 may have a selected sensitivity that is pre-set or configurable as well as a predetermined or configurable measurement range (i.e., a maximum distance at which the sensor 130 detects motion). In some embodiments, the predetermined measurement range is 5 feet or less, 4 feet or less, 3 feet or less, 2 feet or less, 1 foot or less, 9 inches or less, or 6 inches or less inclusive of all intervening and limit values. The measurement range of the sensor 130 may also correspond to, or extend beyond, a distance at which the LEDs 124 are effective at killing viruses and bacteria such that the sensor 130 is able to detect motion at an effective distance of the device 100 generally.

Figure 4:
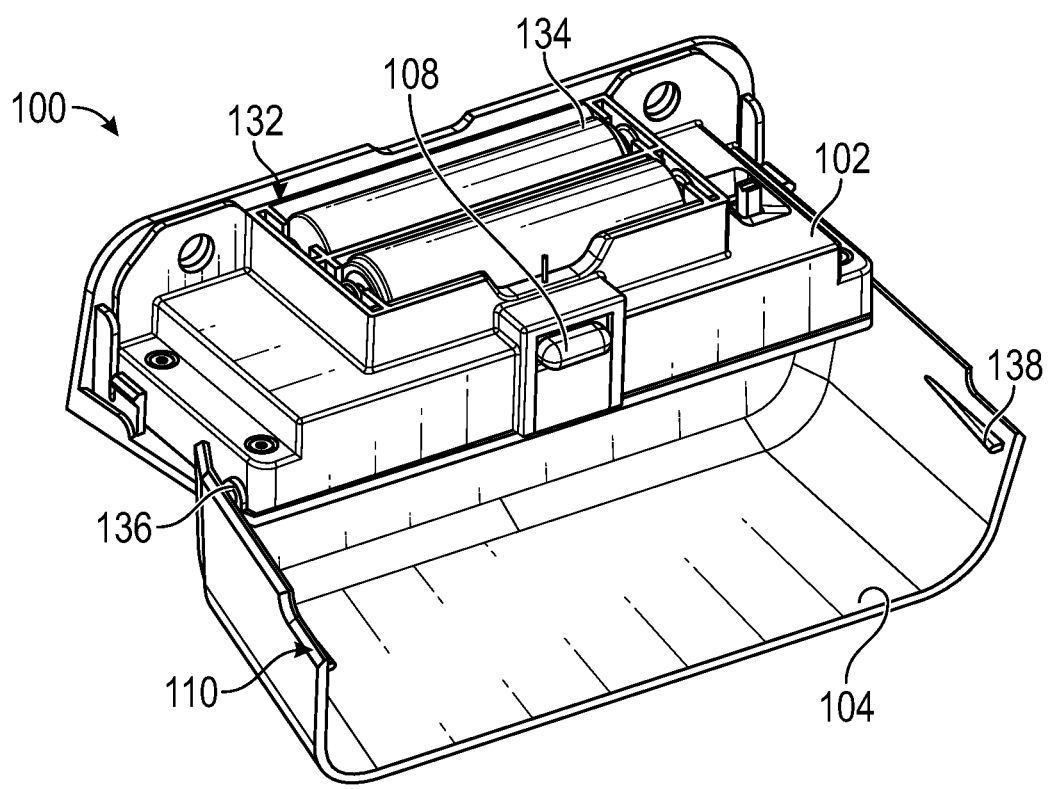
FIG. 4 is a front isometric view of the sanitation device of FIG. 1 with the cover in an open position.

FIG. 4 illustrates the device 100 with the cover 104 rotated to the open position. The housing 102 includes one or more battery terminals 132 that receive rechargeable or replaceable batteries 134 to enable installation and use of the device 100 in additional locations, including locations that are away from external power sources. In an embodiment, the device 100 includes an internal rechargeable battery connectable to an external power source for recharging, or a power input for direct connection to an external power source. The cover 104 is coupled to the housing 102 with hinges 136 that may be pin and barrel hinges. Further, the cover 104 includes engagement protrusions 138 that releasably engage the housing 102 in a snap fit or a force fit connection. Once the device 100 is coupled to a support structure or surface, as described herein, a user can manipulate the cover to an open position via cutouts 110 in the cover 104 and the hinges 136 to replace the batteries 134 or otherwise perform maintenance on the device 100 without having to remove the device from the support surface or support structure.

Thus, the cover 104 is rotatable relative to the housing 102 between open and closed positions. In particular, the cover 104 rotates open and closed to selectively provide access to a battery compartment as well as an ON/OFF switch for the sanitation device 100. The ON/OFF switch may be a toggle switch or some other like device that selectively controls activation or other operational characteristics of the sanitation device 100.

Figure 5:
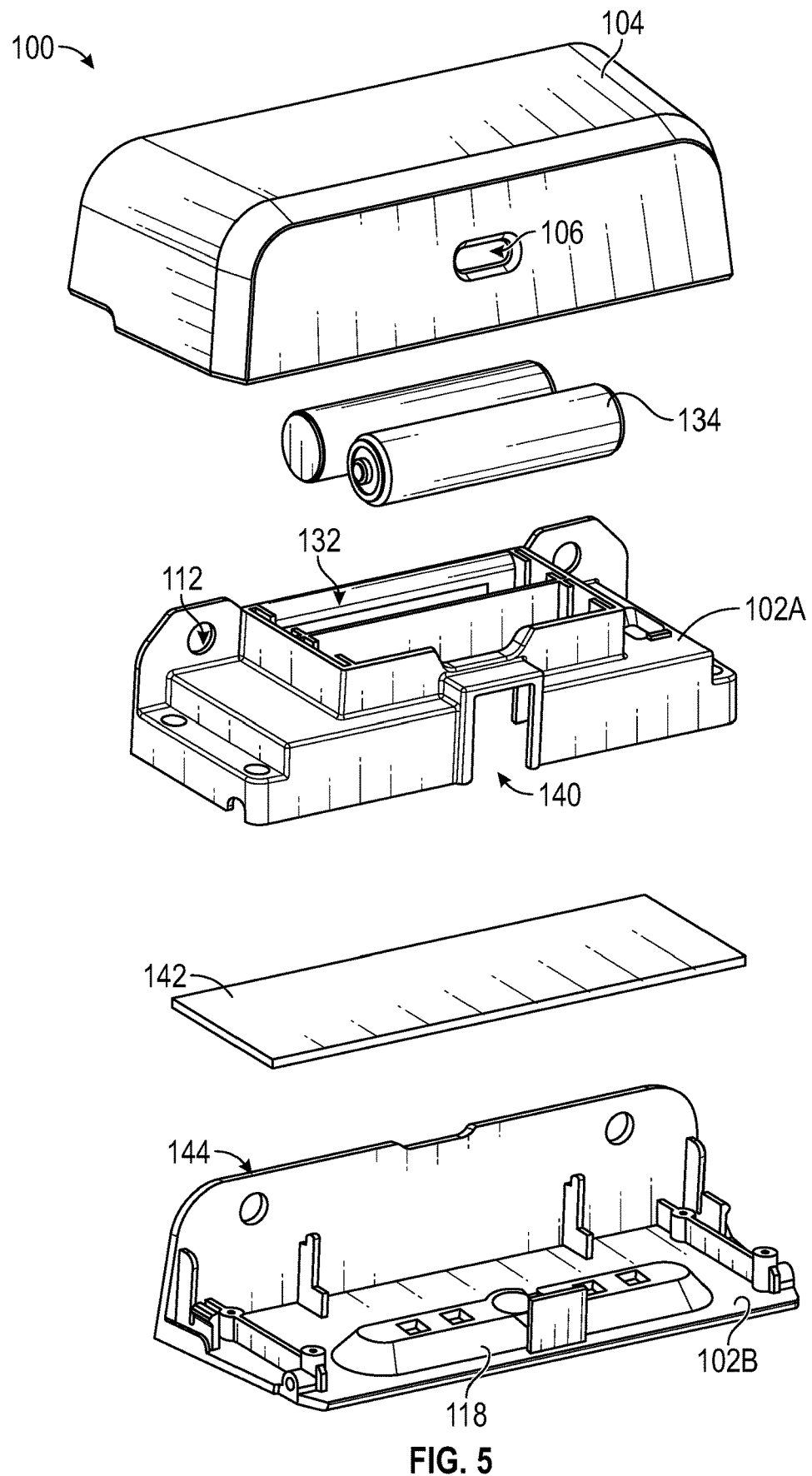
FIG. 5 is an exploded view of the sanitation device of FIG. 1.

Turning to FIG. 5, the housing 102 may be a hollow body with a cover plate 102A coupled to a base 102B with the plate 102A and base 102B cooperating to define an internal cavity 140 for housing various electronic components and hardware of the device 100. In particular, the ON/OFF switch and the batteries 134, as well as other electronic components of the device, are in electronic communication with control circuitry 142 of the sanitation device 100 that is received in the cavity 140. The control circuitry 142 is also in electronic communication with the light emitting diodes 124, the motion detection sensor 130, and the status indicator light 108. The control circuitry 142 is configured to control the operation and function, and selectively provide power from the batteries 134 to, the light emitting diodes 124, the motion detection sensor 130, and the status indicator light 108. The control circuitry 142 will be described in additional detail with reference to FIG. 6. Although the control circuitry 142 is illustrated in FIG. 5 as a blank printed circuit board or some other logic board, it is to be appreciated that various modules, chips, and other like devices are mounted on the board to accomplish the functions described herein. These components can be provided in a number of different form factors, and are described and shown herein schematically for convenience.

The housing 102 may include a cover plate 102A and a base 102B that are coupled together and define the cavity 140, which is internal to the cover plate 102A and the base 102B. The control circuitry 142 is received in the cavity 140. The cover plate 102A of the housing 102, which may be an upper or top portion, may include the battery terminals 132 and the batteries 134, while the base 102B, which may be a lower or bottom portion, includes the channel 118. Either or both of the cover plate 102A and the base 102B may include holes or apertures structured to receive fasteners to couple the sanitation device 100 to an exterior surface.

In some embodiments, a rear surface 144 of the base 102A of the housing 102 includes an adhesive, magnet, or some other adhesive device for coupling the sanitation device 100 to surfaces that have a composition that is not suitable for fasteners, such as porcelain, fiberglass, plastic, stone, metal, or other like materials, as described herein. Such adhesives are best shown in FIG. 2 and may also include a removable cover layer that is removed by the end user in operation before coupling the sanitation device 100 to the exterior surface. The cover plate 102A of the housing 102 includes a step-up configuration to increase the volume of the cavity 140, while also including the battery terminals on an exposed upper surface of the plate 102A so that the batteries 134 are accessible when the cover 104 is in the open position. The base 102B of the housing 102 has an L-shaped configuration with a flat and planar rear surface 144 for mounting to an external support or support surface.

Figure 6:
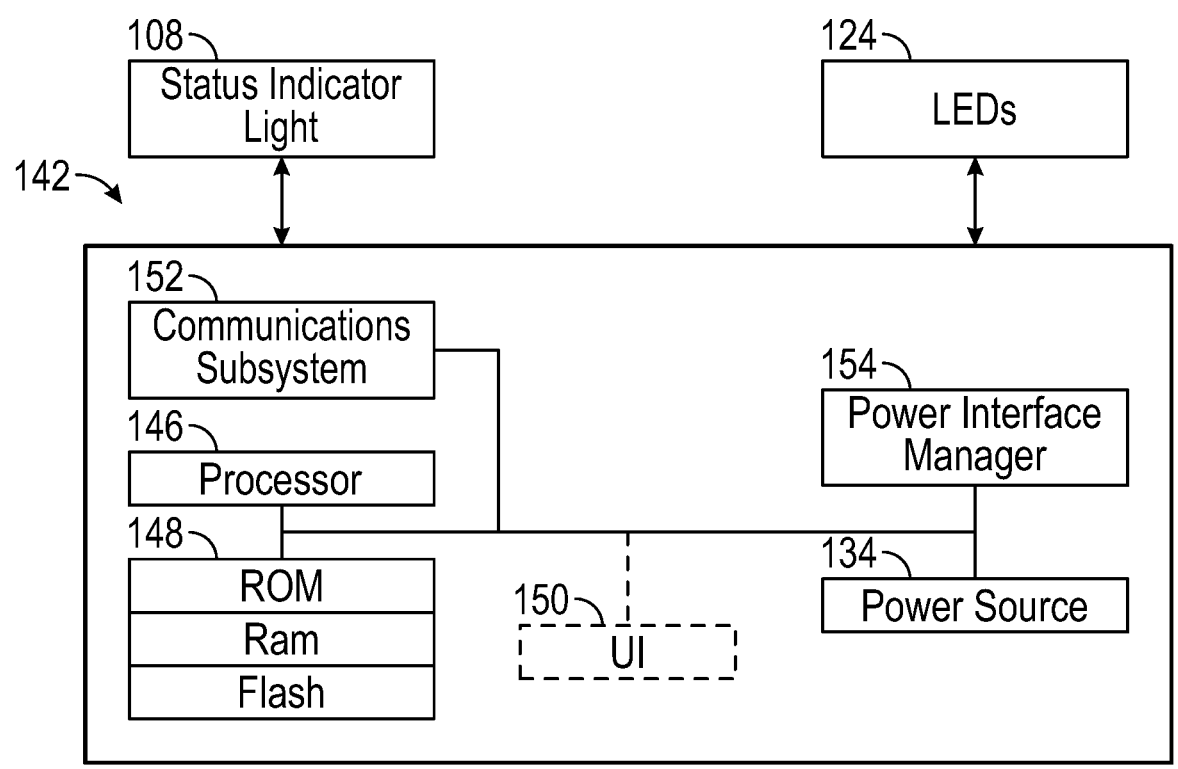
FIG. 6 is a block diagram of control circuitry suitable for executing an embodiment of a sanitation device that performs at least some techniques described in the present disclosure, as well as various devices connected thereto.

FIG. 6 is a block diagram of the control circuitry 142. The control circuitry 142 is generally operable to provide power to the sanitation device 100 from the at least one battery 134, as well as one or more signals or instructions for activation of the various operations and functions of the sanitation device 100 described herein. The control circuitry 142 includes a controller 146 that may be one or more of a microprocessor, a digital signal processor, a programmable gate array (PGA) or an application specific integrated circuit (ASIC). The control circuitry 142 may also include one or more non-transitory storage mediums 148, such as read only memory (ROM), random access memory (RAM), Flash memory, or other physical computer- or processor-readable storage media. The non-transitory storage mediums may store instructions and/or data used by the controller, for example an operating system (OS) and/or applications. The instructions as executed by the controller may execute logic to perform the functionality of the various embodiments of the sanitation devices described herein.

In some embodiments, the controller may include a user interface 150 to allow an end user to operate or otherwise provide input to the sanitation device 100 regarding the operational state or condition of the device. For example, the user interface 150 may include a number of switches or keys operable to turn the sanitation device 100 ON and OFF and/or to set various operating parameters of the sanitation device 100. The user interface 150 may also include one or more auditory transducers, for example one or more speakers and/or microphones. Such may allow audible alert notifications or signals to be provided to an end user, such as when the sanitation device 100 is low on battery or encounters an operational error such as sensor failure in some non-limiting examples.

The switches and keys or the user interface 148 may, for example, include toggle switches or rocker switches. The switches and keys of the user interface 148 may, for example, allow an end user to turn ON the sanitation device 100, turn OFF the sanitation device 100, initiate testing sequences for the light emitting diodes 124 and the motion detection sensor 130, vary the period of time during which the light emitting diodes 124 emit light, vary an intensity or wavelength of light output by the LEDs 124, and vary characteristics of the status indicator light 108 (i.e. output color and illumination duration) in some non-limiting examples.

The control circuitry 142 may include a communications sub-system 152 that may include one or more communications modules or components which facilitate communications with various components of one or more external device, such as a personal computer or processor, etc., in some embodiments. The communications sub-system 152 may provide wireless or wired communications to the one or more external devices. The communications sub-system 152 may include wireless receivers, wireless transmitters or wireless transceivers to provide wireless signal paths to the various remote components or systems of the one or more paired devices. The communications sub-system 152 may, for example, include components enabling short range (e.g., via Bluetooth, near field communication (NFC), or radio frequency identification (RFID) components and protocols) or longer range wireless communications (e.g., over a wireless LAN, Low-Power-Wide-Area Network (LPWAN), satellite, or cellular network) and may include one or more modems or one or more Ethernet or other types of communications cards or components for doing so. The communications sub-system 152 may include one or more bridges or routers suitable to handle network traffic including switched packet type communications protocols (TCP/IP), Ethernet or other networking protocols.

The control circuitry 142 includes a power interface manager 154 that manages supply of power from a power source such as the batteries 134 to the various components of the control circuitry 142 as well as the various components of the sanitation device 100. The power interface manager 154 is coupled to the controller 146 and the power source 134. Alternatively, in some embodiments, the power interface manager 154 can be integrated in the controller. The power interface manager 154 may include power converters, rectifiers, buses, gates, circuitry, etc. In particular, the power interface manager 154 can control, limit, or restrict the supply of power from the power source 134 based on the various operational states of the sanitation device 100.

In some embodiments, the instructions and/or data stored on the non-transitory storage mediums 148 that may be used by the controller 146, such as, for example, ROM, RAM, and Flash memory, includes or provides an application program interface ("API") that provides programmatic access to one or more functions of the control circuitry 142. For example, such an API may provide a programmatic interface to control one or more operational characteristics of the sanitation device 100. Such control may be invoked by one of the other programs, other remote device or system (not shown), or some other module. In this manner, the API may facilitate the development of third-party software, such as various different user interfaces and control systems for other devices, plug-ins, and adapters, and the like to facilitate interactivity and customization of the operation and devices within the sanitation device 100.

In one or more embodiments, components or modules of the control circuitry 142 and other devices within the sanitation device 100 are implemented using standard programming techniques. For example, the logic to perform the functionality of the various embodiments described herein may be implemented as a "native" executable running on the controller 146, e.g., microprocessor, along with one or more static or dynamic libraries. In other embodiments, various functions of the control circuitry 142 may be implemented as instructions processed by a virtual machine that executes as one or more programs whose instructions are stored on ROM and/or RAM. In general, a range of programming languages known in the art may be employed for implementing such embodiments, including representative embodiments of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), or declarative (e.g., SQL, Prolog, and the like).

The embodiments described above may also use well-known or other synchronous or asynchronous client-server computing techniques. However, the various components may be implemented using more monolithic programming techniques as well, for example, as an executable running on a single microprocessor, or alternatively decomposed using a variety of structuring techniques known in the art, including but not limited to, multiprogramming, multithreading, client-server, or peer-to-peer (e.g., Bluetooth®, NFC or RFID wireless technology, mesh networks, etc., running on one or more computer systems each having one or more central processing units (CPUs) or other processors. Some embodiments may execute concurrently and asynchronously, and communicate using message passing techniques. Also, other functions could be implemented and/or performed by each component/module, and in different orders, and by different components/modules, yet still achieve the functions of the control circuitry 142.

In addition, programming interfaces to the data stored on and functionality provided by the control circuitry 142, can be available by standard mechanisms such as through C, C++, C#, and Java APIs; libraries for accessing files, databases, or other data repositories; scripting languages; or Web servers, FTP servers, or other types of servers providing access to stored data. The data stored and utilized by the control circuitry 142 may be implemented as one or more database systems, file systems, or any other technique for storing such information, or any combination of the above, including embodiments using distributed computing techniques.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, and Web Services (XML-RPC, JAX-RPC, SOAP, and the like). Other variations are possible. Other functionality could also be provided by each component/module, or existing functionality could be distributed amongst the components/modules within the sanitation device 100 in different ways, yet still achieve the functions of the control circuitry 142.

Furthermore, in some embodiments, some or all of the components of the control circuitry 142 and components of other devices within the sanitation device 100 may be implemented or provided in other manners, such as at least partially in firmware and/or hardware, including, but not limited to, one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), and the like. Some or all of the system components and/or data structures may also be stored as contents (e.g., as executable or other machine-readable software instructions or structured data) on a computer-readable medium (e.g., as a hard disk; a memory; a computer network, cellular wireless network or other data transmission medium; or a portable media article to be read by an appropriate drive or via an appropriate connection, such as a DVD or flash memory device) so as to enable or configure the computer-readable medium and/or one or more associated computing systems or devices to execute or otherwise use, or provide the contents to perform, at least some of the described techniques.

Various operational states and functionality of the sanitation device 100 are shown in FIGS. 7A-7D. Beginning with FIG. 7A and with continuing reference to FIGS. 1-6, the sanitation device 100 is mounted proximate a common touch point, such as toilet handle 156. The device 100 may be mounted above the toilet handle 156 or other touch point by a selected distance that is preferably within a target effective range of the LEDs 124, such as within 1 inch, 2 inches, 3 inches, 4 inches, 5 inches, 6 inches, 7 inches, 8 inches, 9 inches, 10 inches, 11 inches, 12 inches, or more. The device 100 is activated by the end user toggling the ON/OFF switch to ON. After activation, the processor or microprocessor 146 of the control circuitry 142 executes instructions stored in the memory 148 of the control circuitry 142 to activate the motion detection sensor 130. The processor 146 also executes instructions to activate the status indicator light 108 to emit light in a first color corresponding to a "ready position." In some embodiments, the first color may be green to indicate that the sanitation device 100 is operational and the common touch point is clean.

Figure 7A:
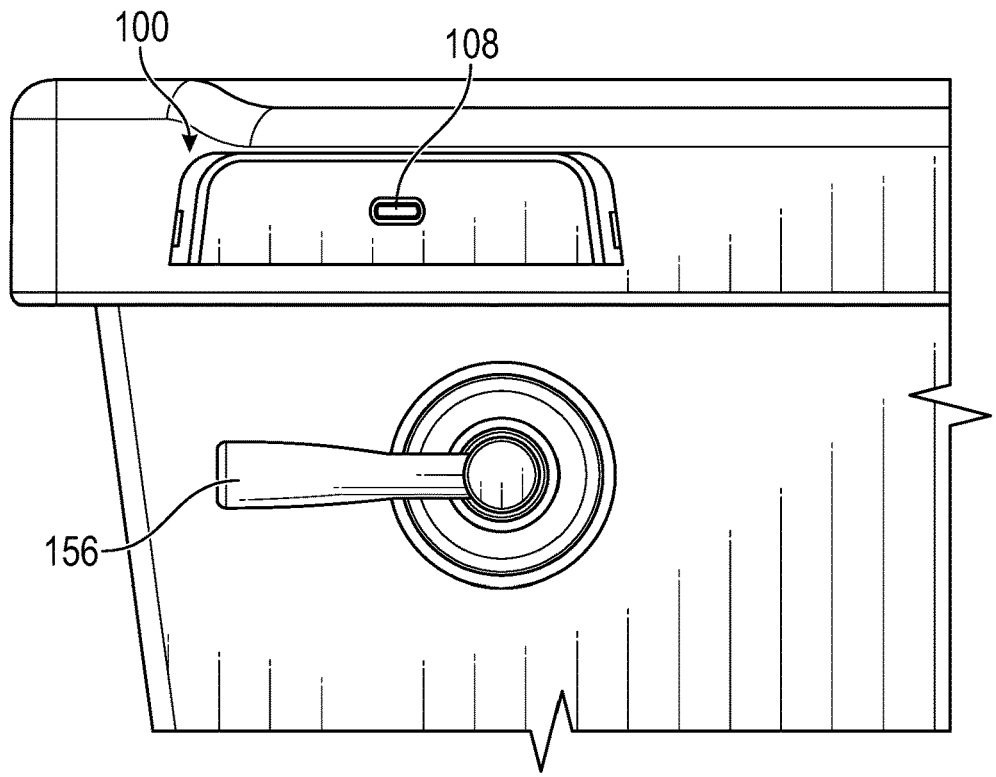
FIGS. 7A-7D are steps in an embodiment of a cleaning process according to the present disclosure.
Figure 7B:
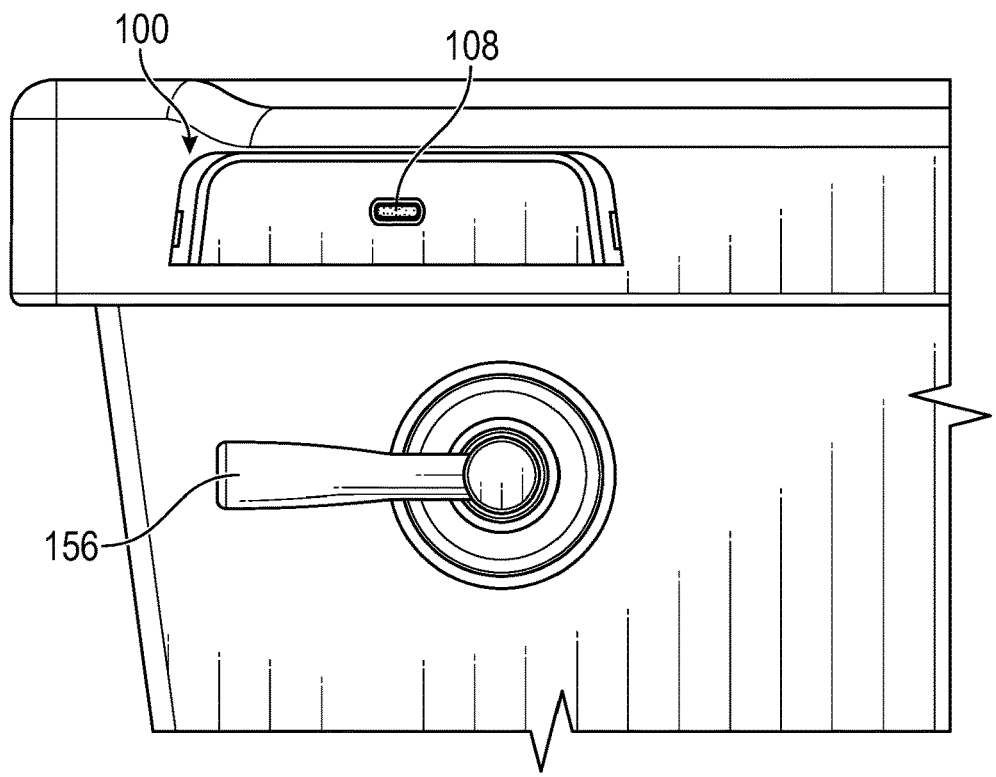
Figure 7C:
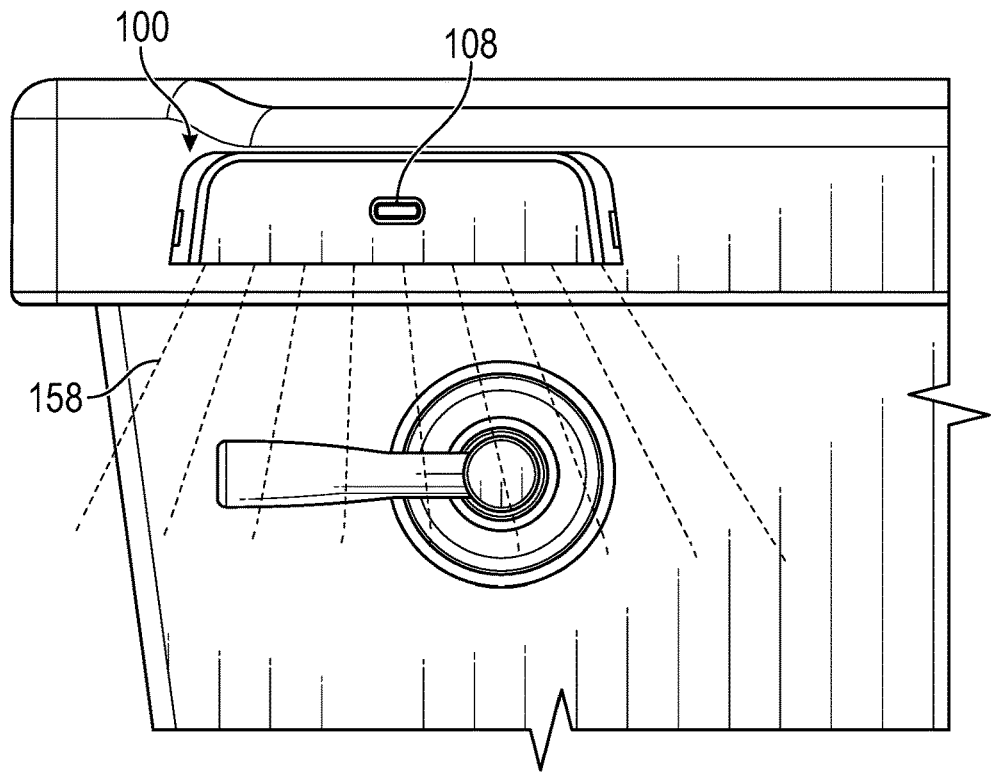

Then, as shown in FIG. 7B, the motion detection sensor 130 determines, via a disruption or detection of infrared light radiating from objects in its field of view, whether an object is proximate the motion detection sensor 130 at a first instance in time. In this non-limiting example, the object could be a user's hand reaching for the handle 156. If so, the control circuitry 142 executes instructions stored in the memory 148 to activate the status indicator light 108 to emit light in a second, different color, such as yellow. The change in the status indicator light 108 represents that the common touch point, such as the handle 156, has recently been touched and therefore may be dirty.

Further, the sensitivity or detection range of the motion detection sensor 130 is tuned to trigger when an end user's hand or other object is within a predetermined range of proximity to the handle. The predetermined range of proximity may be, in some non-limiting examples, 12 inches, 11 inches, 10 inches, 9 inches, 8 inches, 7 inches, 6 inches, 5 inches, 4 inches, 3 inches, 2 inches, or 1 inch, or more or less. The above series of values also includes all integers and decimal values between the listed values. For example, the above series includes 6.5 inches or 6.25 inches, as well as others. Tuning the sensor 130 reduces the likelihood that the sensor 130 will pick up motion away from the handle 156 and thus incorrectly activate the sanitation device 100 even though the handle 156 or common touch point has not been touched.

The shield 126 further assists with limiting the field of view of the sensor 130, as the shield 126 has an outer peripheral edge that extends further from the housing 102 than an outer peripheral edge of the sensor 126. Thus, the sensor 130 is recessed relative to the shield 126 in some embodiments, which limits the field of view of the sensor 130 and prevents the sensor 130 from identifying motion to the side or above the intended field of view. Instead, the sensor 130 is arranged with a vertical view on the handle 156 such that objects which come within the predetermined range of proximity above are detected by the sensor 130.

Then, the sensor 130 determines when the object has moved away from the motion detector sensor 130 at a second instance in time. The second instance in time corresponds to the end user removing their hand from the handle 156 in this non-limiting example. Once the object has moved away from the handle 156, as detected by the sensor 130, the control circuitry 142 executes instructions to begin a sanitation or cleaning process of the common touch point represented by FIG. 7C. Specifically, the control circuitry 142 executes instructions to activate the LEDs 124 to emit UV light onto the common touch point as shown schematically by dashed lines 158 in FIG. 7C. The sidewalls of the channel 118 and the position and angular orientation of the LEDs 124 narrow a field of emission of the LEDs 124 to reduce light leakage and reduce the risk of harm to children, animals, or others who are sensitive to UV light, that may be positioned near the LEDs 124. The control circuitry 142 may execute instructions to activate the LEDs 124 for a set period of time that can be selected based on various factors, such as germicidal capability and power usage per cycle, among others. In some non-limiting examples, the set period of time may be 30 seconds, 20 seconds, 15 seconds, 10 seconds, 5 seconds, or more or less or any period of time between the above values.

Figure 7D:
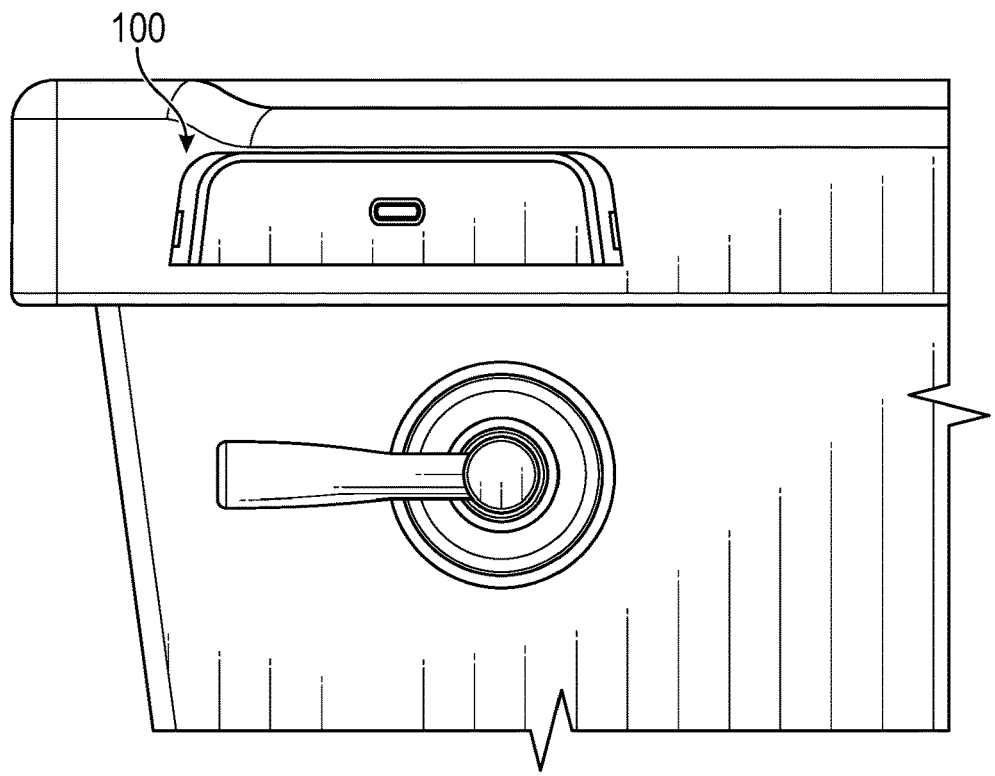

Further, the control circuitry 142 executes instructions to simultaneously activate the status indicator light 108 upon activation of the LEDs 124 to emit light in a third different color, such as red. The third color of the status indicator light 108 represents to users that the sanitation device 100 is in a cleaning cycle and thus they should not place their hand near the touch point. In other words, the third color corresponds to a warning to end users to avoid contact with the UV light output from the LEDs 124. After the expiration of the set period of time, the control circuitry 122 executes instructions to deactivate the LEDs 124 while also executing instructions to activate the status indicator light 108 to emit light in the first, original color as shown in FIG. 7D. Once the status indicator light 108 returns to the first color, the end user is informed that the common touch point is clean and ready for use. The sanitation process described above is repeated indefinitely between uses of the touch point until the batteries are depleted and should be replaced, or some other aspect of the device 100 fails.

In some embodiments, the sanitation device 100 further includes a safety shut-off sensor in electronic communication with the control circuitry 142 and a safety shut-off switch in electronic communication with the safety-shutoff sensor and the control circuitry 142. The safety shut-off sensor may be a motion or proximity sensor that is incorporated into the motion detection sensor 130, or may be a separate and distinct sensor. Put differently, the motion detection sensor may also include, or be programmed to function as, a safety shut-off sensor during operation of the LEDs 124 in one or more embodiments. The control circuitry 142, and more specifically, the processor 146 of the circuitry 142, executes instructions stored in the memory that cause the control circuitry 142 to activate the safety shut-off sensor during operation of the LEDs 124. The control circuitry 142 detects, via the safety shut-off sensor, whether an object is proximate the safety shut-off sensor and/or the LEDs 124 during operation of the plurality of light emitting diodes 124. If so, the control circuitry 142 activates the safety shut-off switch to deactivate the plurality of light emitting diodes 124 in order to protect the end user from the UV-C light as an added safety measure. The range of the safety shut-off sensor can be selected according to design and safety factors and may be the greater than, equal to, or less than the range of the motion detection sensor 130. Thus, the sanitation device 100 also includes functionality to protect the end user if they reach their hand into the UV-C light during operation of the sanitation device 100 via the safety shut-off sensor and safety shut-off switch.

Figure 8:
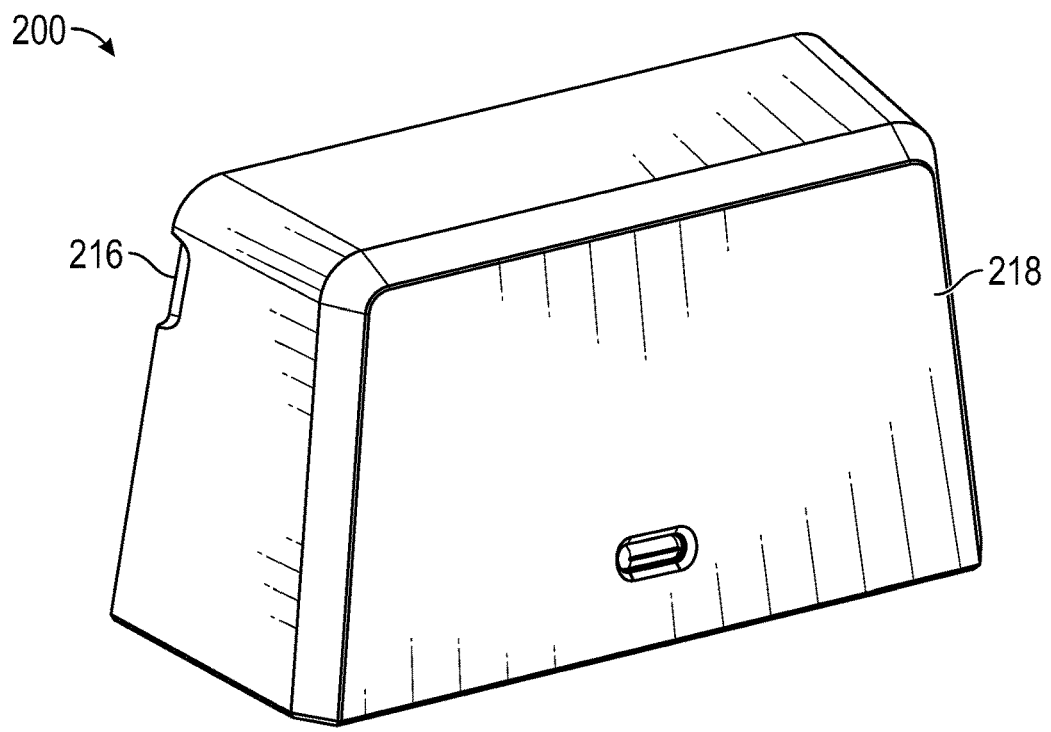
FIGS. 8-11 are various views of an embodiment of a sanitation device according to the present disclosure.
Figure 9:
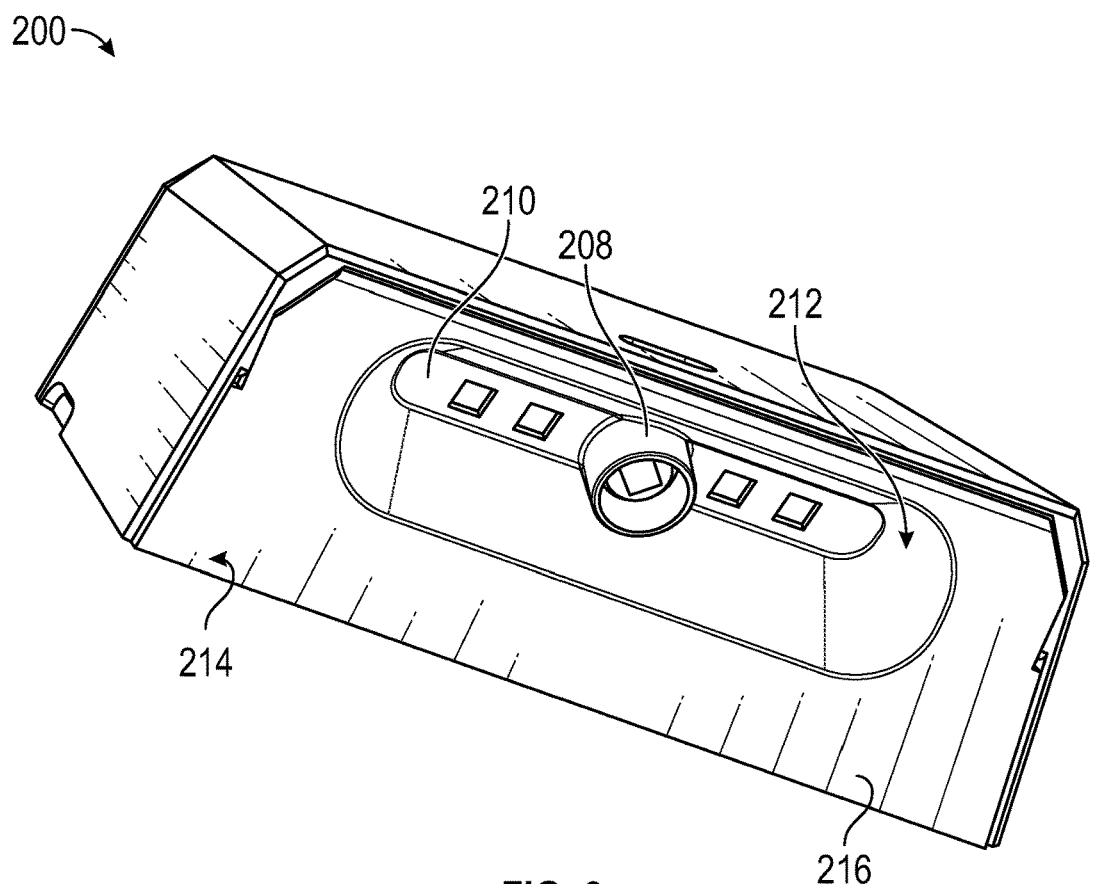
Figure 10:
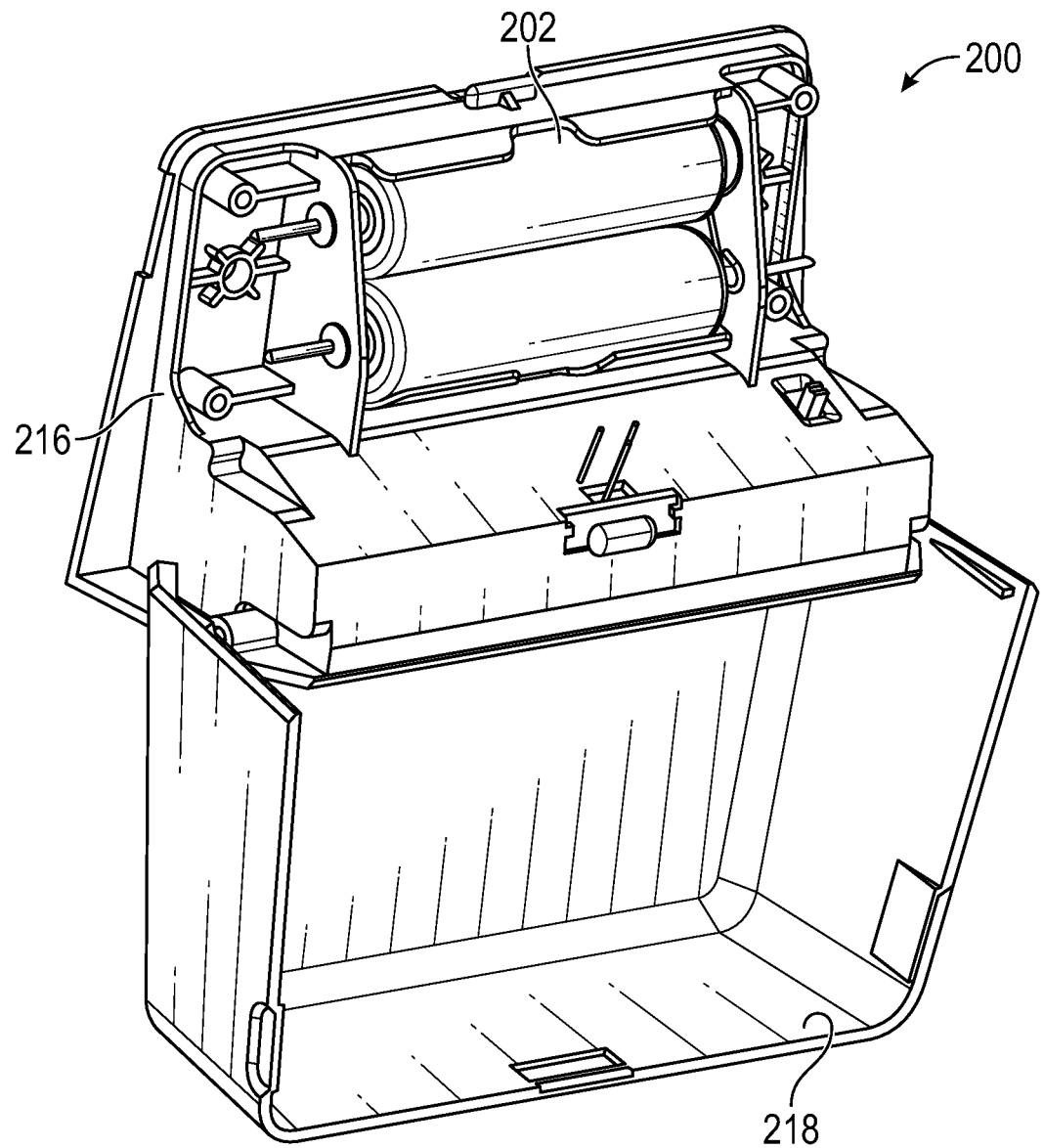
Figure 11:
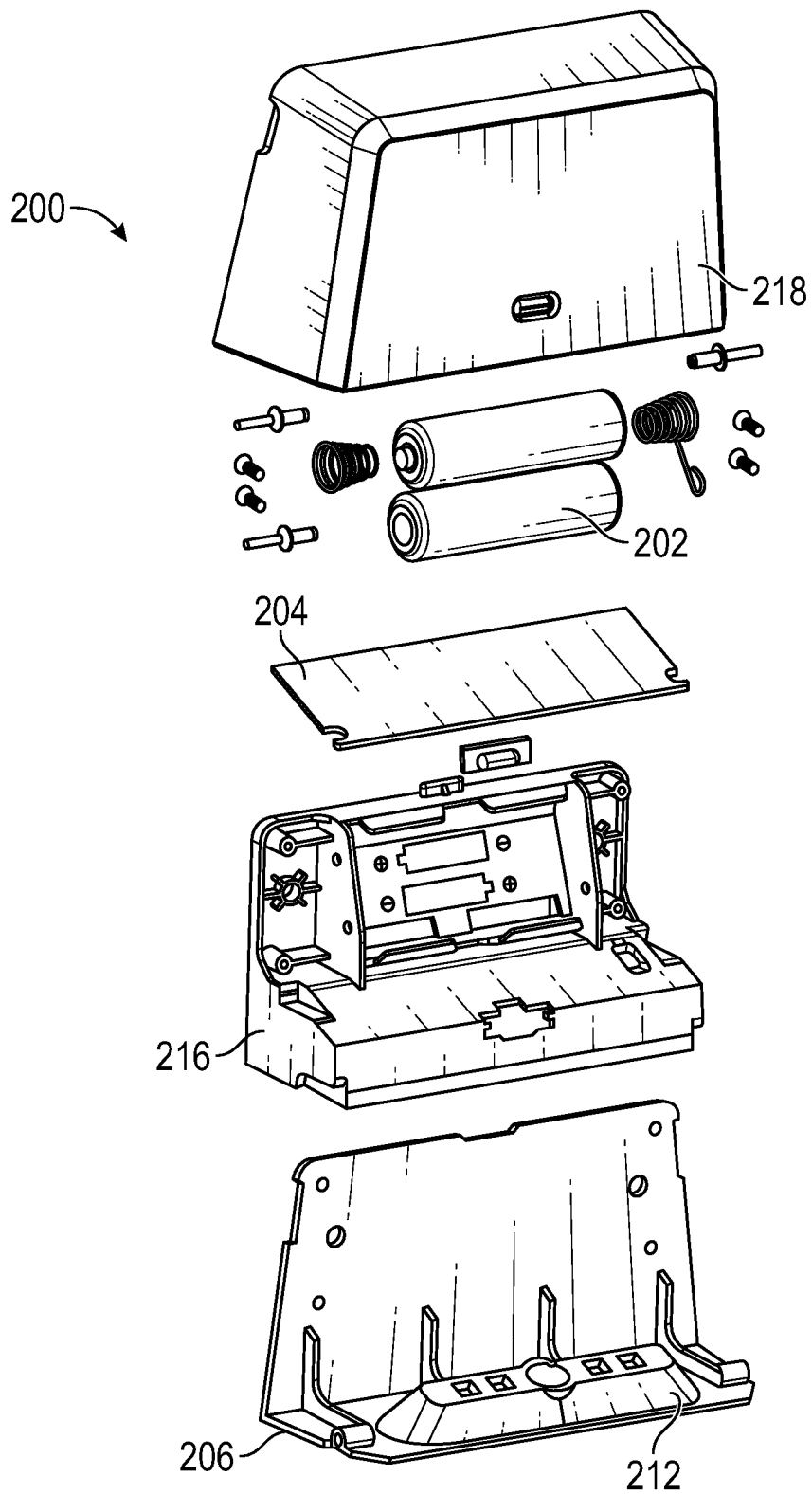

FIGS. 7-10 are various views of an additional embodiment of a sanitation device 200 that may be similar to sanitation device 100, except as otherwise described. More specifically, the sanitation device 200 may include similar features and functionality to sanitation device 100, but with a different form factor. As shown in FIGS. 7-9, the sanitation device 200 may have a taller, slimmer form factor relative to sanitation device 100. Thus, the concepts of the disclosure are not limited to a specific form factor, but rather, can be applied in a number of different forms.

The positions and arrangement of various components of the sanitation device 200 are different to account for the change in form factor. In some non-limiting examples, the device 200 includes batteries 202 that are aligned vertically in device 200 rather than horizontally as in device 100 to reduce the installed width of the device 200. The arrangement of the batteries 202 is best shown in FIG. 9. The device 200 may also include control circuitry 204 that is angled relative to a generally horizontal base 206 of the device 200 to reduce the installed width of the circuitry 204. In addition, the device 200 may include a shield 208 with different dimensions than the shield 126 of device 100. Specifically, the shield 208 may extend further from a base 210 of a channel 212 in a bottom surface 214 of a housing 216, as best shown in FIG. 8. In some embodiments, the outer peripheral edge of the shield 208 that is furthest from the housing 216 is recessed with respect to, planar and aligned with, or extends beyond, a horizontal plane defined by the generally flat and planar bottom surface 214 of the housing 216. The device 200 likewise includes a cover 218 rotatably coupled to the housing 216 to provide access to the batteries 202.

Other features of the sanitation device 200 may be different as well relative to sanitation device 100, such as the number and type of LEDs, the set period of time of activation of the LEDs during the cleaning cycle, the colors output by the status indicator light to represent the various phases of operation, as well as the size, shape, and orientation of the shield, and the type and tuning of the motion detection sensor in some non-limiting examples.

From the foregoing it will be appreciated that, although specific embodiments have been described herein for purposes of illustration, various modifications may be made without deviating from the spirit and scope of the invention. Accordingly, the technology is not limited except by the corresponding claims and the elements recited by those claims. In addition, while certain aspects of the technology may be presented in certain claim forms at certain times, the inventors contemplate the various aspects of the invention in any available claim form.

The above description of illustrated embodiments, including what is described in the Abstract, is not intended to be exhaustive or to limit the implementations to the precise forms disclosed. Although specific embodiments and examples are described herein for illustrative purposes, various equivalent modifications can be made without departing from the spirit and scope of the disclosure, as will be recognized by those skilled in the relevant art. The teachings provided herein of the various embodiments can be applied outside of the sanitation device, system, and method context, and are not limited to the examples generally described above.

For instance, the foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one implementation, the present subject matter may be implemented via Application Specific Integrated Circuits (ASICs). However, those skilled in the art will recognize that the implementations disclosed herein, in whole or in part, can be equivalently implemented in standard integrated circuits, as one or more computer programs executed by one or more computers (e.g., as one or more programs running on one or more computer systems), as one or more programs executed by on one or more controllers (e.g., microcontrollers) as one or more programs executed by one or more processors (e.g., microprocessors), as firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any computer-readable medium for use by or in connection with any processor-related system or method. In the context of this disclosure, a memory is a computer-readable medium that is an electronic, magnetic, optical, or other physical device or means that contains or stores a computer and/or processor program. Logic and/or the information can be embodied in any computer-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "computer-readable medium" can be any element that can store the program associated with logic and/or information for use by or in connection with the instruction execution system, apparatus, and/or device. The computer-readable medium can be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other nontransitory media.

Many of the methods described herein can be performed with variations. For example, many of the methods may include additional acts, omit some acts, and/or perform acts in a different order than as illustrated or described.

Certain words and phrases used in the specification are set forth as follows. As used throughout this document, including the claims, the singular form "a", "an", and "the" include plural references unless indicated otherwise. The terms "include" and "comprise," as well as derivatives thereof, mean inclusion without limitation. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Other definitions of certain words and phrases are provided throughout this disclosure.

The use of ordinals such as first, second, third, etc., does not necessarily imply a ranked sense of order, but rather may only distinguish between multiple instances of an act or a similar structure or material.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other derivatives thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise.

The term "selecting," when used herein in relation to one or more elements of a user interface or other electronic display, may include various user actions taken with respect to various input control devices depending on the client computing device used to interact with the display, such as one or more clicks using a mouse or other pointing device, one or more tapping interactions using a touch screen of a client device, etc. In addition, such selecting may additionally comprise interactions with various physical actuators capable of generating electrical or electronic signals as a result of such interactions. A nonexclusive list of examples of such actuators include electronic, mechanical or electro-mechanical implementations of keys, buttons, pressure plates, paddles, pedals, wheels, triggers, slides, touchpads, or other touch- or motion-sensitive element, and may be digital or analog in nature.

Generally, unless otherwise indicated, the materials for making the invention and/or its components may be selected from appropriate materials such as composite materials, ceramics, plastics, metal, polymers, thermoplastics, elastomers, plastic compounds, and the like.

The foregoing description, for purposes of explanation, uses specific nomenclature and formula to provide a thorough understanding of the disclosed embodiments. It should be apparent to those of skill in the art that the specific details are not required in order to practice the invention. The embodiments have been chosen and described to best explain the principles of the disclosed embodiments and its practical application, thereby enabling others of skill in the art to utilize the disclosed embodiments, and various embodiments with various modifications as are suited to the particular use contemplated. Thus, the foregoing disclosure is not intended to be exhaustive or to limit the invention to the precise forms disclosed, and those of skill in the art recognize that many modifications and variations are possible in view of the above teachings.

The terms "top," "bottom," "upper," "lower," "left," "right," and other like derivatives are used only for discussion purposes based on the orientation of the components in the Figures of the present disclosure. These terms are not limiting with respect to the possible orientations explicitly disclosed, implicitly disclosed, or inherently disclosed in the present disclosure and unless the context clearly dictates otherwise, any of the aspects of the embodiments of the disclosure can be arranged in any orientation.

Unless the context clearly dictates otherwise, relative terms such as "approximately," "substantially," "generally," and other derivatives include an ordinary error range or manufacturing tolerance due to slight differences and variations in manufacturing, and when used to describe a value, amount, quantity, or dimension, generally refer to a value, amount, quantity, or dimension that is within plus or minus 5% of the stated value, amount, quantity, or dimension. It is to be further understood that any specific dimensions of components or features provided herein are for illustrative purposes only with reference to the various embodiments described herein, and as such, it is expressly contemplated in the present disclosure to include dimensions that are more or less than the dimensions stated, unless the context clearly dictates otherwise.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the breadth and scope of a disclosed embodiment should not be limited by any of the above-described embodiments, but should be defined only in accordance with the following claims and their equivalents.

The invention claimed is:

1. A sanitization device, comprising:
   a housing including a cavity and a cover rotatably coupled to the body to selectively provide access to the cavity;
   a channel extending into the housing;
   a plurality of openings in the channel;
   a plurality of light emitting diodes coupled to the housing, wherein the plurality of light emitting diodes emit light through the plurality of openings in the channel when activated;
   a shield coupled to the housing with at least a portion of the shield extending from the channel;
   an aperture in the shield; and
   a motion detection sensor coupled to the housing, wherein the motion detection sensor is able to detect light through the aperture in the shield.

2. The sanitation device of claim 1, wherein the housing further includes a battery terminal, the device further comprising:
   at least one battery received in the battery terminal.

3. The sanitation device of claim 2, wherein the cover of the housing is rotatable to selectively provide access to the battery terminal for replacement of the at least one battery.

4. The sanitation device of claim 2, further comprising:
   control circuitry including a memory and a processor coupled to the housing and positioned in the cavity of the housing, the control circuitry in electronic communication with the at least one battery, the plurality of light emitting diodes, and the motion detection sensor.

5. The sanitation device of claim 4, wherein the processor executes instructions stored in the memory that cause the control circuitry to:
   activate the motion detection sensor;
   determine whether an object is proximate the motion detection sensor at a first instance in time based on the differences in light emitted and detected by the motion detection sensor;

determine when the object has moved away from the motion detection sensor at a second instance in time;

activate the plurality of light emitting diodes for a set period of time in response to the determination that the object has moved away from the motion detection sensor at the second instance; and deactivate the plurality of light emitting diodes after the set period of time.

6. The sanitation device of claim 5, further comprising:
a status indication slot in the cover; and
a status indicator light coupled to the housing, wherein the status indicator light emits light through the status indication slot in the cover, the status indicator light in electronic communication with the control circuitry.

7. The sanitation device of claim 6, wherein the processor executes instructions stored in the memory that cause the control circuitry to:
activate the status indicator light and emit light from the status indicator light in a first color before the first instance;
activate the status indicator light to emit light in a second different color when the object is proximate the motion detector;
activate the status indicator light to emit light in a third different color upon activation of the plurality of light emitting diodes and during the set period of time; and
activate the status indicator light to emit light in the first color after deactivation of the plurality of light emitting diodes after the set period of time.

8. The sanitation device of claim 1, wherein the housing includes a bottom surface, the channel recessed into the bottom surface of the housing with sidewalls of the channel narrowing a field of emission of the plurality of light emitting diodes.

9. The sanitation device of claim 1, wherein the channel has a base and the plurality of light emitting diodes are angled relative to the base of the channel.

10. The sanitation device of claim 1, wherein an outer peripheral edge of the shield extends further from the housing than an outer peripheral edge of the motion detection sensor to narrow a field of view of the motion detection sensor.

11. The sanitation device of claim 1, wherein the motion detection sensor is tuned to trigger based on detection of an object within a predetermined range of proximity to the motion detection sensor.

12. The sanitation device of claim 4, further comprising:
a safety shut-off sensor in electronic communication with the control circuitry; and
a safety shut-off switch in electronic communication with the safety-shutoff sensor and the control circuitry.

13. The sanitation device of claim 12, wherein the processor executes instructions stored in the memory that cause the control circuitry to:
activate the safety shut-off sensor during operation of the plurality of light emitting diodes;
detect with the safety shut-off sensor whether an object is proximate the safety shut-off sensor during operation of the plurality of light emitting diodes; and
activate the safety shut-off switch to deactivate the plurality of light emitting diodes upon detection that the object is proximate the safety shut-off sensor during operation of the plurality of light emitting diodes.

14. The sanitation device of claim 12, wherein the motion detection sensor includes the safety shut-off sensor.

15. A sanitization device, comprising:
a housing;
a channel extending into the housing;
a plurality of light emitting diodes coupled to the housing and operable to emit light from the channel;
a shield coupled to the housing and positioned in the channel, the shield including an aperture; and
a motion detection sensor coupled to the housing and operable to detect light through the aperture in the shield.

16. The sanitation device of claim 15, wherein the housing includes a cavity, the sanitation device further comprising:
a plurality of openings in the channel, the plurality of light emitting diodes operable to emit light through the plurality of openings in the channel; and
a cover rotatably coupled to the housing to selectively provide access to the cavity of the housing.

17. The sanitation device of claim 15, further comprising:
control circuitry including a memory and a processor coupled to the housing, the control circuitry in electronic communication with the plurality of light emitting diodes and the motion detection sensor, wherein the processor executes instructions stored in the memory that cause the control circuitry to:
activate the motion detection sensor;
determine whether an object is proximate the motion detection sensor at a first instance in time based on the differences in light emitted and detected by the motion detection sensor;
determine when the object has moved away from the motion detection sensor at a second instance in time;
activate the plurality of light emitting diodes for a set period of time in response to the determination that the object has moved away from the motion detection sensor at the second instance; and
deactivate the plurality of light emitting diodes after the set period of time.

18. The device of claim 17, further comprising:
a status indication slot in the cover; and
a status indicator light coupled to the housing, wherein the status indicator light emits light through the status indication slot in the cover, the status indicator light in electronic communication with the control circuitry,
wherein the processor executes instructions stored in the memory that cause the control circuity to:
activate the status indicator light and emit light from the status indicator light in a first color before the first instance;
activate the status indicator light to emit light in a second different color when the object is proximate the motion detector;
activate the status indicator light to emit light in a third different color upon activation of the plurality of light emitting diodes and during the set period of time; and
activate the status indicator light to emit light in the first color after deactivation of the plurality of light emitting diodes after the set period of time.

19. The sanitation device of claim 17, further comprising:
a safety shut-off sensor in electronic communication with the control circuitry; and
a safety shut-off switch in electronic communication with the safety-shutoff sensor and the control circuitry, wherein the processor executes instructions stored in the memory that cause the control circuity to:
activate the safety shut-off sensor during operation of the plurality of light emitting diodes;

detect with the safety shut-off sensor whether an object is proximate the safety shut-off sensor during operation of the plurality of light emitting diodes; and activate the safety shut-off switch to deactivate the plurality of light emitting diodes upon detection that the object is proximate the safety shut-off sensor during operation of the plurality of light emitting diodes.

20. The sanitation device of claim 15, wherein the housing includes a bottom surface, the channel recessed into the bottom surface of the housing with sidewalls of the channel narrowing a field of emission of the plurality of light emitting diodes, and wherein the channel has a base and the plurality of light emitting diodes are angled relative to the base of the channel.

\* \* \* \* \*